US00PP31777P2

(12) United States Plant Patent
van den Haak

(10) Patent No.: US PP31,777 P2
(45) Date of Patent: May 19, 2020

(54) ***ANEMONE* PLANT NAMED 'IFANFJ'**

(50) Latin Name: *Anemone hupehensis*
Varietal Denomination: IFANFJ

(71) Applicant: Jelle van den Haak, Amsterdam (NL)

(72) Inventor: Jelle van den Haak, Amsterdam (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 16/501,264

(22) Filed: Mar. 14, 2019

(51) Int. Cl.
*A01H 5/02* (2018.01)
*A01H 6/72* (2018.01)

(52) U.S. Cl.
USPC ..... Plt./263.1

(58) Field of Classification Search
USPC ..... Plt./263.1
CPC ..... A01H 6/72; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Anemone* plant named 'IFANFJ', characterized by its upright and uniform plant habit; moderately vigorous growth habit; early and freely flowering habit; long flowering period; large single type flowers that are red purple in color; and good garden performance.

2 Drawing Sheets

Botanical designation: *Anemone hupehensis.*
Cultivar denomination: 'IFANFJ'.

BACKGROUND OF THE INVENTION

The present invention relates to a new and distinct cultivar of *Anemone*, botanically known as *Anemone hupehensis* and hereinafter referred to by the name 'IFANFJ'.

The new *Anemone* plant is a product of a planned breeding program conducted by the Inventor in Heerhugowaard, The Netherlands. The objective of the breeding program is to create new compact and vigorous *Anemone* plants with numerous attractive flowers.

The new *Anemone* plant originated from a cross-pollination made by the Inventor in September, 2012 in Heerhugowaard, The Netherlands of a proprietary selection of *Anemone hupehensis* identified as code number 148-10-K001-01, not patented, as the female, or seed, parent with a proprietary selection of *Anemone hupehensis* identified as code number 148-10-K004-01, not patented, as the male, or pollen, parent. The new *Anemone* plant was discovered and selected by the Inventor as a single flowering plant within the progeny of the stated cross-pollination in a controlled greenhouse environment in Heerhugowaard, The Netherlands in September, 2013.

Asexual reproduction of the new *Anemone* by in vitro meristem culture in a controlled environment in Heerhugowaard, The Netherlands since April, 2014 has shown that the unique features of this new *Anemone* plant are stable and reproduced true to type in successive generations.

SUMMARY OF THE INVENTION

Plants of the new *Anemone* have not been observed under all possible combinations of environmental conditions and various cultural practices. The phenotype may vary somewhat with variations in environmental conditions such as temperature and light intensity without, however, any variance in genotype.

The following traits have been repeatedly observed and are determined to be the unique characteristics of 'IFANFJ'. These characteristics in combination distinguish 'IFANFJ' as a new and distinct *Anemone* plant:

1. Upright and uniform plant habit.
2. Moderately vigorous growth habit.
3. Early and freely flowering habit.
4. Long flowering period.
5. Large single type flowers that are red purple in color.
6. Good garden performance.

Plants of the new *Anemone* can be compared to plants of the female parent selection. Plants of the new *Anemone* differ primarily from plants of the female parent selection in the following characteristics:

1. Plants of the new *Anemone* have single type flowers whereas plants of the female parent selection have double type flowers.
2. Flowers of plants of the new *Anemone* are larger than flowers of plants of the female parent selection.

Plants of the new *Anemone* can be compared to plants of the male parent selection. Plants of the new *Anemone* differ primarily from plants of the male parent selection in the following characteristics:

1. Flowers of plants of the new *Anemone* are larger than flowers of plants of the male parent selection.
2. Plants of the new *Anemone* have longer flowering stems than plants of the male parent selection.

Plants of the new *Anemone* can be compared to plants of *Anemone hupehensis* 'Cinderella', disclosed in U.S. Plant Pat. No. 25,367. In side-by-side comparisons, plants of the new *Anemone* and 'Cinderella' differ primarily in the following characteristics:

1. Flowers of plants of the new *Anemone* are larger than flowers of plants of 'Cinderella'.

2. Flowers of plants of the new *Anemone* are more intense red purple in color than flowers of plants of 'Cinderella'.
3. Plants of the new *Anemone* have longer flowering stems than plants of 'Cinderella'.

BRIEF DESCRIPTION OF THE PHOTOGRAPHS

The accompanying colored photographs illustrate the overall appearance of the new *Anemone* plant showing the colors as true as it is reasonably possible to obtain in colored reproductions of this type. Colors in the photographs may differ slightly from the color values cited in the detailed botanical description which accurately describe the colors of the new *Anemone* plant.

The photograph on the first sheet is a side perspective view of a typical plant of 'IFANFJ' in a container.

The photograph at the top of the second sheet comprises a close-up view of typical flowers and flower buds of 'IFANFJ'.

The photograph at the bottom of the second sheet comprises a close-up view of typical leaves of 'IFANFJ'.

DETAILED BOTANICAL DESCRIPTION

The aforementioned photographs and following observations, measurements and values describe plants grown during the summer in 17-cm containers in an outdoor nursery in Heerhugowaard, The Netherlands and under cultural practices typical of commercial *Anemone* production. During the production of the plants, day temperatures ranged from 10° C. to 25° C. and night temperatures ranged from 4° C. to 15° C. Plants were 15 weeks old when the photographs and description were taken. In the following description, color references are made to The Royal Horticultural Society Colour Chart, 2015 Edition, except where general terms of ordinary dictionary significance are used.

Botanical classification: *Anemone hupehensis* 'IFANFJ'.

Parentage:

*Female, or seed, parent*.—Proprietary selection of *Anemone hupehensis* identified as code number 148-10-K001-01, not patented.

*Male, or pollen, parent*.—Proprietary selection of *Anemone hupehensis* identified as code number 148-10-K004-01, not patented.

Propagation:

*Type*.—In vitro meristem culture.

*Time to initiate roots, summer*.—About ten days at temperatures about 22° C.

*Time to initiate roots, winter*.—About 15 days at temperatures about 20° C.

*Time to produce a rooted young plant, summer*.—About 42 days at temperatures about 20° C.

*Time to produce a rooted young plant, winter*.—About 50 days at temperatures about 20° C.

*Root description*.—Fine, fibrous; close to N199C to N199D in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Herbaceous perennial; upright and uniform plant habit with basal stems and leaves developing in basal rosettes; numerous basal rosettes developing per plant; obovate in overall plant shape; moderately vigorous growth habit; moderate growth rate.

*Plant height, soil level to top of foliar plane*.—About 22 cm.

*Plant height, soil level to top of floral plane*.—About 40 cm.

*Plant diameter*.—About 37 cm.

Branch description:

*Quantity per plant*.—About 23.

*Length*.—About 13 cm.

*Diameter*.—About 3.5 mm.

*Strength*.—Strong.

*Aspect*.—Upright to about 5° from vertical.

*Texture and luster*.—Densely pubescent; moderately glossy.

*Color*.—Initially, close to 144B becoming closer to 144A with development.

Leaf description:

*Arrangement, basal leaves*.—Alternate; compound.

*Arrangement, cauline leaves*.—Opposite; simple to compound.

*Length, basal leaves*.—About 7.7 cm.

*Width, basal leaves*.—About 8.1 cm.

*Length, cauline leaves*.—About 7.4 cm.

*Width, cauline leaves*.—About 5.1 cm.

*Length, basal and cauline leaflets*.—About 5.3 cm.

*Width, basal and cauline leaflets*.—About 3.1 cm.

*Shape, basal leaves*.—Broadly ovate; palmately trifoliate; depth of sinuses are medium to very deep and convergent.

*Shape, cauline leaves*.—Ovate; palmately trifoliate; depth of sinuses are medium to very deep and convergent.

*Shape, basal and cauline leaflets*.—Ovate.

*Apex, basal and cauline leaves and leaflets*.—Acute.

*Base, basal leaves and leaflets*.—Cuneate.

*Base, cauline leaves and leaflets*.—Attenuate.

*Margin, basal and cauline leaves and leaflets*.—Biserrate.

*Aspect, basal and cauline leaves and leaflets*.—Mostly flat to slightly convex.

*Texture and luster, basal and cauline leaves and leaflets, upper surface*.—Sparsely pubescent; slightly glossy.

*Texture and luster, basal and cauline leaves and leaflets, lower surface*.—Sparsely pubescent; matte.

*Venation pattern, basal and cauline leaves and leaflets*.—Laciniate.

*Color, basal and cauline leaves and leaflets*.—Developing leaves and leaflets, upper surface: Close to 144A. Developing leaves and leaflets, lower surface: Close to 144B. Fully expanded leaves and leaflets, upper surface: Close to NN137A; venation, close to 143B. Fully expanded leaves and leaflets, lower surface: Close to 147B; venation, close to 144B.

*Leaf petioles*.—Length, basal leaves: About 11.4 cm. Diameter, basal leaves: About 2 mm. Length, cauline leaves: About 2.7 cm. Diameter, cauline leaves: About 2 mm by 1.5 mm. Strength, basal and cauline leaves: Strong. Texture and luster, basal and cauline leaves, upper and lower surfaces: Sparsely to moderately pubescent; slightly glossy. Color, basal and cauline leaves, upper surface: Close to 146B. Color, basal and cauline leaves, lower surface: Close to 146A.

*Stipules*.—To date, stipule development has not been observed on plants of the new *Anemone*.

Flower description:

*Flower arrangement and flowering habit*.—Single type rotate flowers arranged in terminal compound cymes; freely flowering habit with 115 flowers developing per plant during the flowering season; flowers face mostly upright to slightly outwardly.

*Fragrance*.—None detected.

*Natural flowering season*.—Plants of the new *Anemone* flower during the late summer into the autumn in The Netherlands.

*Flower longevity*.—Individual flowers last about one week on the plant; flowers not persistent.

*Inflorescence height*.—About 23.4 cm.

*Inflorescence diameter*.—About 15.9 cm.

*Flower diameter*.—About 5.3 cm.

*Flower length* (*depth*).—About 1.5 cm.

*Flower buds*.—Length: About 1 cm. Diameter: About 8 mm. Shape: Ovoid. Texture and luster: Densely pubescent; matte. Color: Close to 186C; proximally, close to 145B.

*Petals*.—Absent.

*Sepals*.—Quantity and arrangement: About five or six arranged in a single whorl. Length: About 2.7 cm. Width: About 2.4 cm. Shape: Elliptic to obovate; moderately concave. Apex: Obtuse. Base: Cuneate. Margin: Entire; slightly to moderately undulate. Texture and luster, upper surface: Smooth, glabrous; moderately velvety; matte. Texture and luster, lower surface: Densely pubescent; matte. Color: When opening and fully opened, upper surface: Close to 70A to 70B; venation, close to 70A; color does not change with development. When opening and fully opened, lower surface: Close to 70B; venation, close to 70B; colors does not change with development.

*Peduncles*.—Length: About 13.6 cm. Diameter: About 2.5 mm. Aspect: About 20° from vertical. Strength: Strong. Texture and luster: Moderately pubescent; moderately glossy. Color: Close to 143A to 143B; distally, strongly tinged with close to 187A.

*Pedicels*.—Length: About 7.9 cm. Diameter: About 1.5 mm. Aspect: About 25° from the peduncle axis. Strength: Moderately strong. Texture and luster: Densely pubescent; slightly glossy. Color: Close to 148A; upper surface tinged with between 187A and 200A.

*Flower bracts*.—To date, flower bract development has not been observed on plants of the new *Anemone*.

*Reproductive organs*.—Androecium: Stamen number per flower: About 200. Filament length: About 4.5 mm. Filament color: Close to 157C. Anther shape: Oblong. Anther length: About 1.5 mm. Anther diameter: About 0.5 mm. Anther color: Close to 17C. Amount of pollen: Abundant. Pollen color: Close to 11D. Gynoecium: Pistil number per flower: About 400. Pistil length: About 1 mm. Stigma shape: Club-shaped. Stigma length: About 0.5 mm. Stigma diameter: About 0.5 mm. Stigma color: Close to N144B. Style length: About 0.5 mm. Style color: Close to 150D. Ovary color: Close to 144A.

*Seeds and fruits*.—To date, seed and fruit development have not been observed on plants of the new *Anemone*.

Garden performance: Plants of the new *Anemone* have been observed to have good garden performance, to tolerate high temperatures of about 35° C. and to be suitable for USDA Hardiness Zones 4 through 9.

Pathogen & pest resistance: To date, plants of the new *Anemone* have not been observed to be resistant to pathogens and pests common to *Anemone* plants.

It is claimed:

1. A new and distinct *Anemone* plant named 'IFANFJ' as illustrated and described.

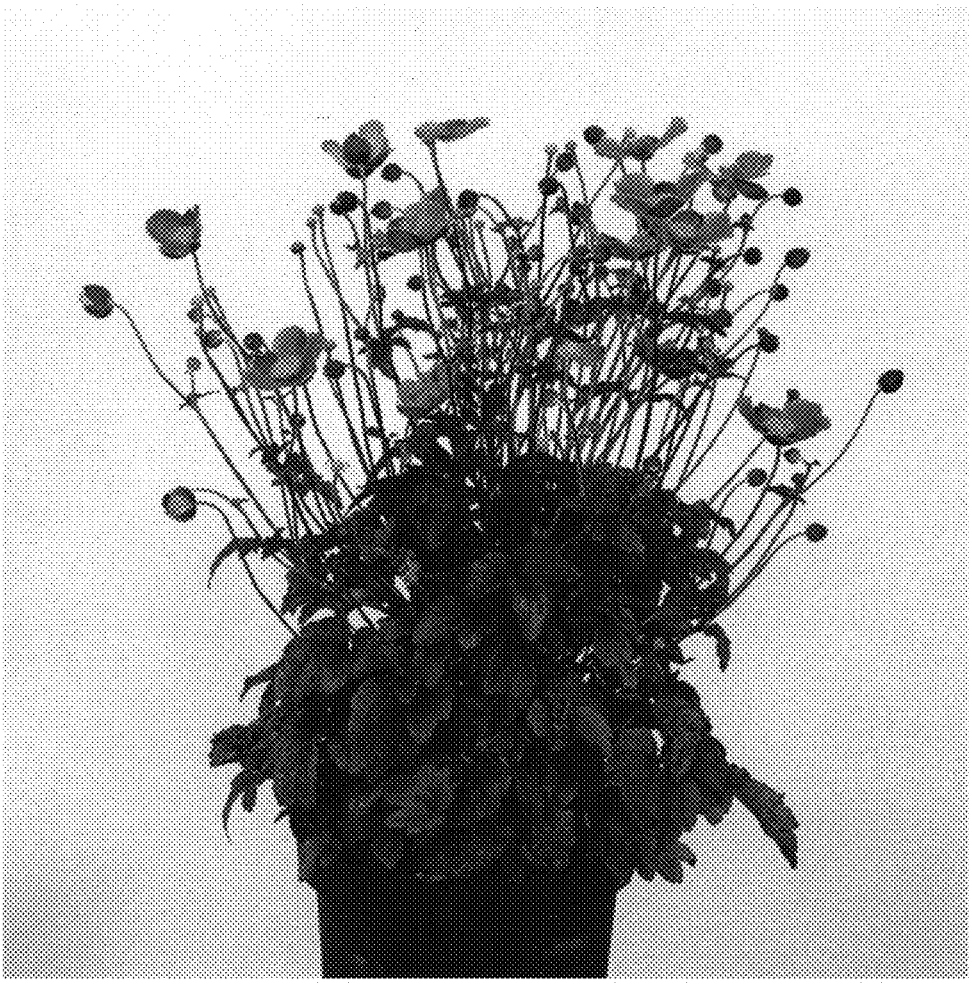

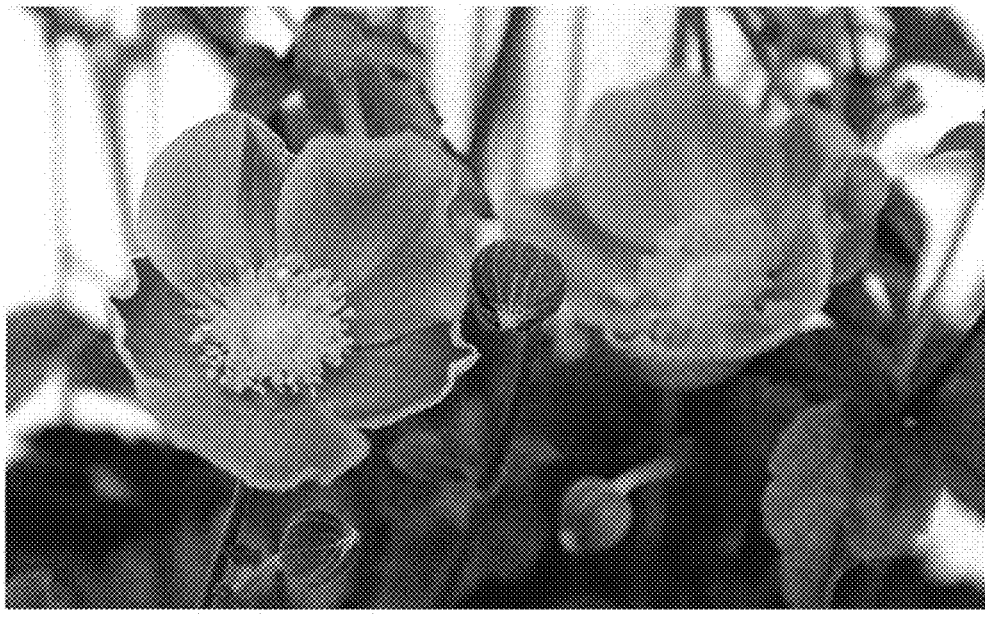
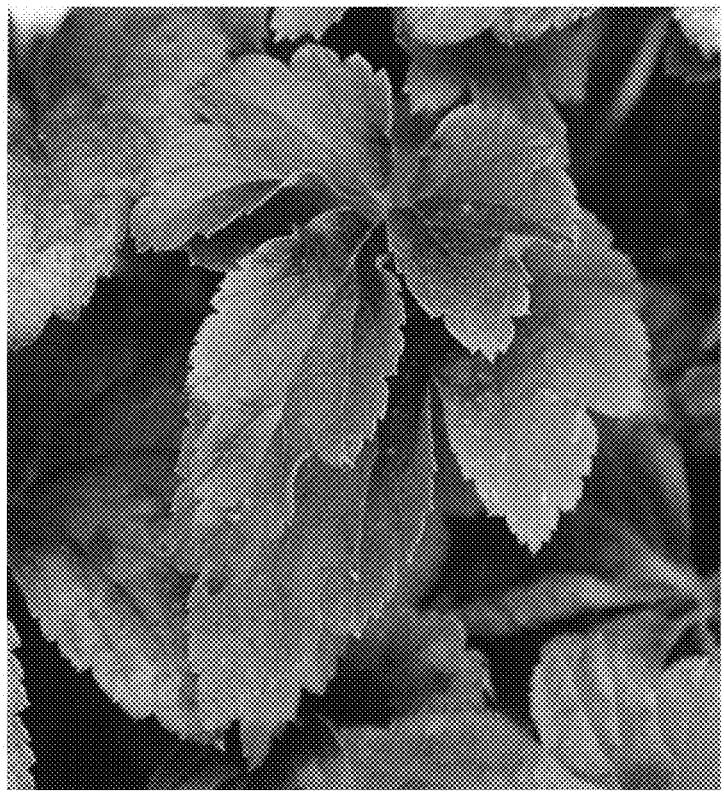

* * * * *